United States Patent [19]

Chapel

[11] 4,438,977
[45] Mar. 27, 1984

[54] APPARATUS FOR REMOVING MATERIAL

[76] Inventor: Nimrod T. Chapel, 3804 Green Oaks Way, Edmond, Okla. 73034

[21] Appl. No.: 264,635

[22] Filed: May 18, 1981

Related U.S. Application Data

[63] Continuation-in-part of Ser. No. 113,192, Jan. 18, 1980, Pat. No. 4,274,676.

[51] Int. Cl.³ .......................... A47L 7/02; E01H 1/08
[52] U.S. Cl. ........................................ 299/64; 299/12; 15/321; 15/345; 51/273
[58] Field of Search ............... 299/12, 81, 64; 15/321, 15/322, 345; 134/4, 6; 252/88; 51/273

[56] References Cited

U.S. PATENT DOCUMENTS

| | | | |
|---|---|---|---|
| 1,821,715 | 9/1931 | Kuchinsky | 15/322 |
| 2,319,023 | 5/1943 | Walker | 51/180 |
| 2,463,455 | 3/1949 | Dann | 164/32 |
| 2,514,142 | 7/1950 | Reid | 15/322 X |
| 2,701,559 | 2/1955 | Cooper | 73/425 X |
| 3,041,793 | 7/1962 | Shimizu | 51/180 |
| 3,110,182 | 11/1963 | Moss et al. | 73/421 X |
| 3,134,127 | 5/1964 | Klein | 15/321 |
| 3,460,294 | 8/1969 | Stumpf | 51/273 X |
| 3,598,446 | 8/1971 | Hatcher | 299/39 |
| 3,606,470 | 9/1971 | Blum | 299/64 X |
| 3,608,968 | 9/1971 | Burnett | 299/39 |
| 3,690,727 | 9/1972 | Degginger | 252/88 X |
| 3,843,198 | 10/1974 | Reynolds | 299/64 |
| 3,954,662 | 5/1976 | Salyer et al. | 252/88 X |

FOREIGN PATENT DOCUMENTS

| | | | |
|---|---|---|---|
| 448760 | 10/1946 | Canada | 252/88 |
| 316737 | 8/1929 | United Kingdom | 118/35 |
| 807537 | 10/1957 | United Kingdom | 299/81 |
| 1259898 | 1/1972 | United Kingdom | 51/273 |

Primary Examiner—Ernest R. Purser
Attorney, Agent, or Firm—E. Harrison Gilbert, III

[57] ABSTRACT

An apparatus for removing material from a surface so that the removed material will not escape into the ambient environment is disclosed. The present invention includes a coagulant-applying mechanism for spraying a coating of coagulant on the material to be removed. Also included is a cutter head assembly which is moved along the surface for scraping the material therefrom. So that the scraped, coagulated material may be safely withdrawn to a storage receptacle, the present invention also includes a mechanism which withdraws the loosened, coagulated particles from the cutter head assembly.

3 Claims, 7 Drawing Figures

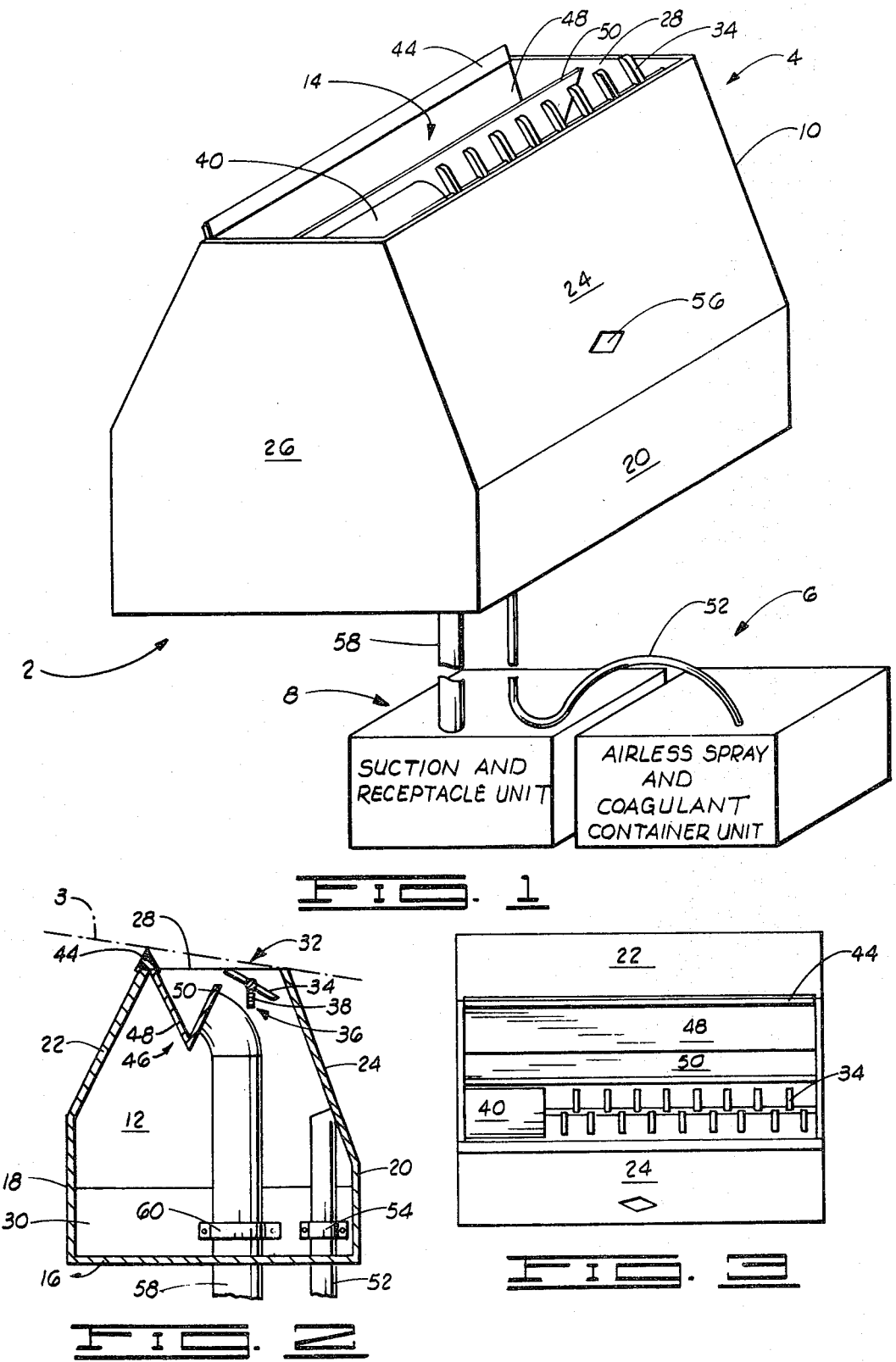

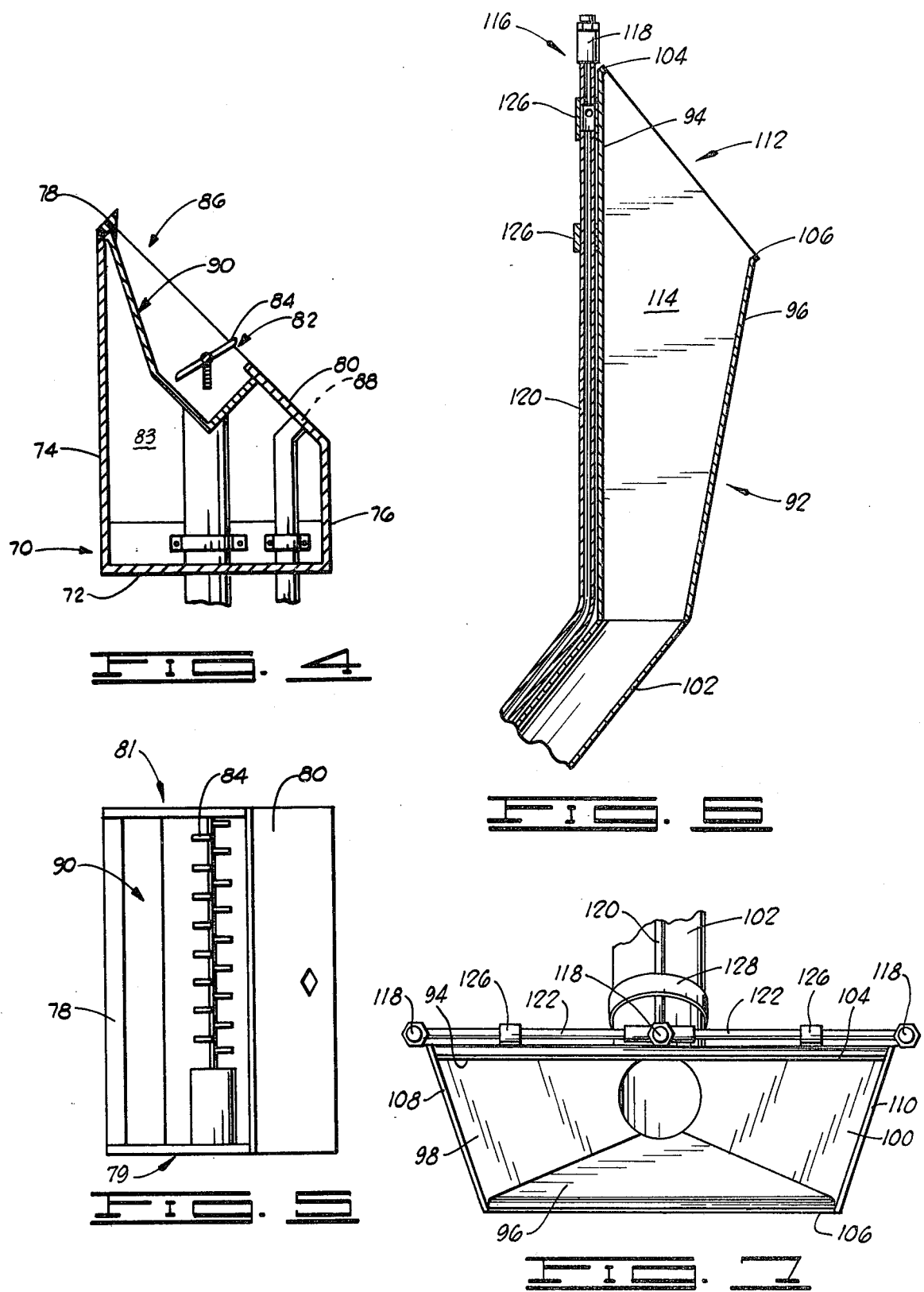

APPARATUS FOR REMOVING MATERIAL

REFERENCE TO RELATED APPLICATION

This is a continuation-in-part of application Ser. No. 113,192 filed Jan. 18, 1980 now U.S. Pat. No. 4,274,676.

BACKGROUND OF THE INVENTION

This invention relates generally to apparatus for removing material and more particularly, but not by way of limitation, to apparatus for removing asbestos from walls without contaminating the ambient environment.

It is often necessary to remove various materials from their natural or fabricated locations, such as rock formations or interior building walls. For example, it is currently necessary to remove deposits of asbestos found in building materials which have been used in such places as schools. This necessity for asbestos removal has arisen from the discovery that asbestos is, or may be, a carcinogen. Thus, there is the need for an apparatus which can remove the desired materials by cutting, scraping, or otherwise removing, them from the desired locations.

To prevent the removed material from dispersing throughout the ambient environment and thereby possibly causing contamination, such as could occur with particles of asbestos, it is necessary to perform removal without allowing the removed particles arising from the cutting or other removing process to filter into the ambient environment. Thus, there is the need for the apparatus to contain the removed particles, such as by coagulating the particles into a bonded mass, and to withdraw them from the removal area.

That there is the general need for an apparatus for cutting or scraping a surface and removing the material therefrom is supported by U.S. Pat. No. 3,843,198 in the name of Reynolds. This patent discloses a rock sampling tool which cuts the rock from a surface and which uses an air stream to reduce dispersal of resultant dust into the surrounding area.

Although the Reynolds patent discloses such a device, it will be noted that individual particles of dust resulting from the rock cutting operation may escape into the ambient environment without being drawn into the air stream of Reynolds' device because of the tendency of certain substances to scatter or disperse upon being cut, scraped, or otherwise loosened. This is a critcal shortcoming when the material to be removed is asbestos, for example, because the escape of even a few particles of asbestos can create a serious health hazard.

SUMMARY OF THE INVENTION

The present invention overcomes the above-noted and other shortcomings of the prior art by providing a novel, useful and non-obvious apparatus for removing material. This invention can be used to remove materials from the structures in which the materials are used. In particular, the present invention provides an apparatus for removing asbestos without allowing a significant amount, if any, of the removed particles to filter into the ambient environment. The apparatus provides for containing the removed particles and for withdrawing these particles from the area from which they are removed.

Broadly, the present invention provides an apparatus for removing material from a surface comprising means for applying a coating of a coagulant to the material to be removed; means, associated with the coagulant applying means, for scraping the surface to loosen the material therefrom; and means, associated with the scraping means, for withdrawing the loosened material from the scraped surface.

More particularly, the coagulant applying means includes means for airlessly spraying a substance and a coagulant container coupled with the airlessly spraying means so that the coagulant is extracted from the container by the spraying means and airlessly sprayed on the material to be removed.

The scraping means includes a housing and a cutter member rotatably connected to the housing for striking the material to be removed when the housing is moved adjacent the surface.

The withdrawing means includes means for creating a suction and a conduit extending from the suction means to a position proximate the cutter member for receiving the loosened material and conveying it to the suction means.

Therefore, from the foregoing, it is a general object of the present invention to provide a noval apparatus for removing material. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is an oblique and block illustration of the removal apparatus of the present invention.

FIG. 2 is a sectional end elevation view of the cutter head assembly shown in FIG. 1.

FIG. 3 is a top plan view of the cutter head assembly shown in FIG. 1.

FIG. 4 is a sectional end elevation view of a second embodiment of a cutter head assembly of the present invention.

FIG. 5 is a top plan view of the cutter head assembly shown in FIG. 4.

FIG. 6 is a sectional end elevation view of a third embodiment of a cutter head assembly of the present invention.

FIG. 7 is a top plan view of the cutter head assembly shown in FIG. 6.

DETAILED DESCRIPTION OF THE PREFERRED EMBODIMENTS OF THE INVENTION

With reference now to the drawings and in particular to FIGS. 1–3, a preferred embodiment of the removal apparatus constructed in accordance with the present invention will be described. In FIG. 1 the apparatus for removing material from a surface, which apparatus is particularly for removing asbestos from a surface 3 and for preventing the removed asbestos particles from escaping into the ambient environment by using a coagulant, is generally identified by the reference numeral 2. The apparatus 2 includes means 4 for scraping the surface to loosen the material therefrom, means 6 for applying a coating of a coagulant to the material to be removed, and means 8 for withdrawing the loosened, coagulant-coated material from the scraped surface.

In the preferred embodiment, the scraping means 4 is a cutter head assembly comprising a housing 10. As shown in FIG. 2, the housing 10 includes a cavity 12 extending into the housing from an opening 14 formed in the wall of the housing 10. In the preferred embodiment the housing 10 is to be constructed of a lightweight stainless steel and is from six to twenty-four inches long, twelve inches wide and twelve inches high. However, the material and size may be of any appropriate nature suitable for practicing the present invention.

For the preferred embodiment shown in FIGS. 1-3, the housing 10 includes a bottom wall 16, a first side wall 18 connected along an edge thereof to one edge of the bottom wall 16 in perpendicular relationship with the bottom wall 16 such that in the preferred embodiment the side wall 18 extends vertically from the bottom wall 16 when the bottom wall 16 is horizontal, and a second side wall 20 connected along an edge thereof to the edge of the bottom wall 16 opposite that edge from which the first side wall 18 extends in perpendicular relationship with the bottom wall 16 such that in the preferred embodiment the side wall 20 extends vertically from the bottom wall 16 when the bottom wall 16 is horizontal. The housing 10 further includes a third side wall 22 angularly extending from another edge of the first side wall 18, which edge is disposed opposite the edge of the side wall 18 connected to the first edge of the bottom wall 16, inwardly toward the opening 14 defined adjacent the top edge of the third side wall 22. The housing 10 also includes a fourth side wall 24 extending angularly from another edge of the second side wall 20, which other edge is disposed opposite the edge of the side wall 20 connected to the second edge of the bottom wall 16, inwardly toward the opening 14 defined also adjacent the top edge of the fourth side wall 24. Connected to the ends of the connected side walls and bottom wall are a first end wall 26 and a second side wall 28. This assemblage of the bottom wall 16, the side walls 18, 20, 22 and 24, and the end walls 26 and 28 defines the cavity 12. Disposed within the cavity 12 and extending between the first side wall 18 and the second side wall 20 is a support plate 30.

The cutter head assembly also includes a cutter member 32 having one or more blades 34 extending therefrom. The member 32 is rotatably connected to the end walls 26 and 28 of the housing 10 so that the blade 34 extends through the opening 14 when the member 32 rotates. Having the blade 34 extend through the opening permits it to scrape the surface from which the desired material is to be removed. That is, as the housing 10 is moved along the surface from which the material is to be removed, the cutter member 32 rotates and the blade 34 strikes the material on and below the surface to thereby dislodge the material therefrom. The blade or blades 34 may be placed on the cutter member 32 in any appropriate position, such as in the staggered, or offset, configuration shown in FIG. 3.

FIG. 2 also shows that the present invention includes mounting means having a biasing element for yieldably receiving the cutter member 32. In particular the preferred embodiment mounting means includes a groove formed in each of the end walls 26 and 28 of the housing 10 to extend vertically downward from the rotatably mounted cutter member 32. Located within each of the grooves 36 is a biasing element such as a spring 38. One end of the spring 38 is held adjacent the bottom surface of the groove 36 and the opposite end of the spring 38 yieldably retains the rotatably mounted cutter member 32 thereon. Thus, the mounting means permits the cutter member 32 to be vertically displaced by a downwardly acting force which exceeds the biasing force of the spring 38. This means for permitting the vertical displacement of the cutter member helps keep the cutter member 32 from binding when irregularities are encountered on the surface along which the cutter head assembly is moved. In the preferred embodiment the mounting means permits approximately one inch of vertical displacement.

The present invention further includes drive means for rotating the cutter member. In particular the drive means includes a motor 40 as represented in FIG. 1. The energization of the motor 40 can be from a battery pack located within the cutter head assembly or it can be provided by another energization means remotely located but connected to the motor via conductors extending therebetween.

FIG. 2 further shows that the preferred embodiment shown therein includes a resilient member 44 extending along the top edge of the third side wall 22. Particularly, the resilient member 44 is a rubber strip extending along one edge of the opening 14 and above the plane containing the opening 14, i.e., above the outer surface of the wall of the housing in which the opening 14 is defined. The resilient member 44 provides means for sealing the cutter head assembly against the surface from which the material is to be removed so that the material will not escape as the cutter member 32 rotates its blade 34 toward the member 44. In the preferred embodiment the resilient member 44 is a three-quarter-inch rubber strip extending one-half inch above the top surface of the housing 10 and along the entire length thereof.

As just described, the resilient member 44 provides a seal between the cutter head assembly and the surface which is being scraped so that the loosened material will not pass between a gap which might otherwise be formed between the surface and the head assembly. By so sealing this head/surface interface, the loosened material is caused to fall into a trough 46 which is connected to the side wall 22 so that the trough extends into the cavity 12 below the cutter member 32. Thus, as the cutter member 32 and blade 34 rotate to cut into the surface 3, the loosened material scraped from the surface is collected in the trough 46. In the preferred embodiment the trough 46 extends approximately three inches below the top edge of the side wall 22 to which the upper edge of the trough 46 is connected. As shown in FIG. 2, the preferred embodiment trough 46 has a V-shaped configuration as defined by the connection of a first leg 48 and a second leg 50.

As depicted in FIG. 1, the means for applying a coating of coagulant to the material includes means for airlessly spraying a substance and also includes a container of the coagulant coupled with the airlessly spraying means so that the coagulant is extracted from the container by the spraying means and airlessly sprayed on the material to be removed.

The airlessly spraying means includes a substance discharging means which may be of any suitable type as known in the art for airlessly spraying a substance. As shown in FIG. 1, coupled with and extending from the discharging means is a first conduit 52 of any type suitable for use in an airless spraying system. The discharging end of the first conduit 52 is connected to the housing 10. In particular, as shown in FIG. 2, the conduit 52 is passed through an opening in the bottom wall 16 and is connected to the plate 30 by means of a bracket 54 so that the discharging end of the conduit 52 is held in position adjacent an outlet port 56, defined in the fourth side wall 24, to airlessly discharge the coagulant pumped by the discharging means therethrough.

The coagulant container is of any suitable type as known in the art. The coagulant is a stabilizing substance which causes the particles of the removed material to become bonded as integral parts of a bonded mass which will not disperse into the ambient enviroment, but rather will fall into the cavity 12 of the housing 10. One example of the coagulant is a suitable mixture of a high molecular weight polyamide and water.

The means for withdrawing the loosened material from the scraped surface, which means is associted with the scraping means 4, includes means for creating a suction, such as any appropriate vacuum device as known in the art, and a conduit 58 coupled to the suction creating means and extending therefrom, through an opening in the bottom wall 16, and to a position proximate the cutter member 32 for receiving the loosened material and conveying it to a receptacle contained within the suction means. As shown in FIG. 2, the inlet end of the conduit 58 is connected to the trough 46, and in particular to the leg 50 thereof, so that as the coagulated particles of the removed material fall into the trough 46 they are withdrawn therefrom by means of a suction generated by the suction creating means. The conduit 58 may be of any suitable type, but in the preferred embodiment it is contemplated to be a flexible tube having a diameter of from approximately two to three inches. The conduit 58 is held in position adjacent the trough 46 by means of a bracket 60 which clamps the conduit 58 to the plate 30. Although the preferred embodiment shows the conduit 58 connected to the trough 46, it is to be noted that the present invention can properly operate by merely disposing the inlet end of the conduit 58 in the cavity 12 and allowing the removed particles to fall into the cavity whereby they are withdrawn through the conduit 58 under suction provided by the suction creating means.

Referring to FIGS. 4 and 5, a second preferred embodiment of the scraping means, or cutter head assembly, of the present invention will be briefly discussed. In this embodiment, the cutter head assembly includes a housing 70 comprising a bottom wall 72, a first side wall 74 extending vertically, or more generally, perpendicularly from one of the edges of the bottom wall 72, and a second side wall 76 extending vertically or, more generally, perpendicularly from the opposite edge of the bottom wall 72. The housing 70 also includes a resilient member 78 and a first angular side wall 80 extending from the first side wall 74 and the second side wall 76, respectively. The resilient member 78 and the angular side wall 80 correspond to elements 44 and 24, respectively, of the first embodiment described above. A first end wall 79 and a second end wall 81 are connected to respective ends of the walls 72, 74, 76 and 80 so that a cavity 83 is defined thereby.

The FIG. 4 embodiment also includes a cutter member 82 having one or more blades 84 extending therefrom similar to the corresponding elements in the preceding embodiment. However, in the FIG. 4 embodiment the cutter element 82 and the blade 84 are disposed within the housing 70 so that the blade 84 extends through an opening 86 defined between the unconnected edges of the member 78 or side wall 74 and the side wall 80 in substantially the same plane as the angular side wall 80 and an outlet port 88 defined in the side wall 80 and through which the coagulant is dischargable by the coagulant applying means of the present invention. In other words, the coagulant is discharged and the cutting is performed along the same planar surface of the housing 70 of the second preferred embodiment of the present invention. Also shown in FIG. 4 is a trough 90 shown extending from the side wall 74 to the side wall 80 beneath the cutter member 82.

A third embodiment of a portion of the present invention is shown in FIGS. 6 and 7. This embodiment includes a housing 92 defined by a first side wall 94, a second side wall 96, a first end wall 98 and a second end wall 100. Each of the side and end walls is connected, such as by welding or other suitable means, at a respective end to a neck member 102. The side walls 94 and 96 extend away from the neck member 102 at obtuse included angles with respect to the neck member 102, and the side walls 94 and 96 diverge from each other at an acute angle so that the included angle between the side wall 94 and the neck member 102 is less oblique (i.e., of smaller degree) than the included angle between the side wall 96 and the neck member 102. Stated differently, the obtuse included angle defined by the side wall 96 and the neck member 102 is greater than the obtuse included angle between the side wall 94 and the neck member 102. The end walls 98 and 100 diverge from each other at an acute angle in the preferred embodiment.

The side wall 94 extends farther away from the neck member 102 than does the side wall 96 so that a line extending from an outer edge 104 of the side wall 94 to an outer edge 106 of the side wall 96 defines an acute angle with respect to the side wall 94 and an obtuse angle with respect to the side wall 96. The end wall 98 has an outer edge 108 which extends from one end of the edge 104 to an end of the edge 106, and the end wall 100 has an outer edge 110 which extends from the other end of the edge 104 to the other end of the edge 106. The edges 104, 106, 108, and 110 terminate the side and end walls in a peripheral edge which defines an opening 112 having a substantially trapezoidal shape. The edges 104, 106, 108, and 110 are coplanar so that the opening 112 defined thereby lies in a plane extending in angular relationship with respective surfaces of the first and second side walls 94 and 96.

The opening 112 provides access to a cavity 114 formed in the housing 92. The cavity 114 has substantially trapezoidally shaped cross-sections which decrease with the depth of the cavity 114. The trapezoidal shape is formed because the end members 98 and 100 extend from respective side edges of the side wall 94 to respective side edges of the side wall 96 so that acute included angles are defined between the end walls 98 and 100 and the side wall 94 and obtuse included angles are defined between the end walls 98 and 100 and the side wall 96. The decrease in size results from the convergence or funneling of the side and end walls toward the neck member 102 (or, in other words, from the divergence of the side and end walls away from the neck member 102).

The neck member 102 connects by suitable conduit means (not shown) with the suction creating means of the present invention so that particles entering the cavity 114 are safely withdrawn therefrom. The particles contemplated to enter the cavity 114 are those which are scraped by suitable scraping means which can be mounted in the housing 92 similarly to those illustrated in FIGS. 1–5.

To prevent or reduce the chances of the scraped particles escaping into the environment outside the cavity 114, the third embodiment includes nozzle means 116 for emitting the coagulant substance discharged by the substance discharging means of the airless spraying means. The preferred embodiment nozzle means 116 includes a plurality of spray beads 118 which are connected to a common conduit 120 by means of branch conduits 122. The common conduit 120 connects with a suitable conduit (not shown) extending from the substance discharging means. The conduits 120 and 122 are attached to the external surface of the side wall 94 by suitable retaining means, such as brackets 126. The conduit 120 is retained adjacent the external surface of the neck member 102 by suitable means, such as a retaining band 128. The direction of the spray emitted from the spray beads 118 is substantially to the right as viewed in FIG. 6.

The construction of the foregoing embodiments permits the present invention to be relatively easily used to safely apply coagulant to the surface, scrape the surface, and contain and withdraw the material scraped from the surface.

The operation of the present invention will be described initially with reference to the embodiment shown in FIGS. 1–3. The side 24 of the cutter head assembly is first moved adjacent the surface from which the particular material is to be removed. During this step of moving the cutter head assembly, the coagulant is discharged from the discharging means through the conduit 52 and the outlet port 56 so that a coating of the coagulant is applied to the surface containing the material to be removed. After the material has been coated with the coagulant, the top portion of the cutter head assembly is moved adjacent the surface so that the cutter member 32 and the blade 34 extending therefrom engage the surface to cut, and thereby loosen, the material therefrom. During this cutting step the resilient member 44 is maintained in engagement with the surface to insure that the loosened, coagulant-coated material falls into the cavity 12 of the housing 10. As the cutter blades 34 loosen the material and the material falls into the cavity 12, the trough 46 collects this material so that it can be withdrawn from the cutter head assembly by means of the conduit 58 and the suction creating means connected thereto. Thus, as the loosened material falls into the cutter head assembly, it is withdrawn into a receptacle provided within the suction creating means.

When the cutting process is completed, all the loosened, coagulant-coated material is contained in the receptacle of the suction means. Therefore, by first applying the coagulant to the material to be removed, and then loosening it from its location, the loosened particles are prevented from escaping into the ambient environment and thus are prevented from creating possible health hazards if the loosened material is of a possibly dangerous nature, as with asbestos.

The embodiment illustrated in FIGS. 4 and 5 operates similarly to the one described in FIGS. 1–3. However, one difference is that both the coagulation application and the material cutting steps are performed substantially simultaneously because both of these operations are performed by means disposed along a single surface of the cutter head assembly.

The embodiment shown in FIGS. 6–7 functions similarly to the embodiment shown in FIGS. 4–5 in that the coagulant application and the material cutting and withdrawing steps can be accomplished during single passes of the cutter head assembly across the substance to be removed. In this embodiment the neck member 102 can function as a handle by which the housing 92 can be moved across the substance to be removed.

Thus, the present invention of an apparatus for removing material is well adapted to carry out the objects and attain the ends and advantages mentioned above as well as those inherent therein. While preferred embodiments of the invention have been described for the purpose of this disclosure, numerous changes in the construction and arrangement of parts can be made by those skilled in the art, which changes are encompassed within the spirit of this invention as defined by the appended claims.

What is claimed is:

1. An apparatus for removing material from a surface, comprising:
    scraping means for scraping the surface to loosen the material therefrom, said scraping means having a cavity and an opening defined therein and including:
        a bottom wall;
        a first side wall connected along an edge thereof to a first edge of said bottom wall;
        a second side wall connected along an edge thereof to a second edge of said bottom wall, said second edge disposed opposite said first edge of said bottom wall;
        a third side wall angularly extending from another edge of said first side wall, which other edge of said first side wall is disposed opposite the edge of said first side wall connected to said first edge of said bottom wall, said third side wall extending inwardly toward said opening;
        a fourth side wall angularly extending from another edge of said second side wall, which other edge of said second side wall is disposed opposite the edge of said second side wall connected to said second edge of said bottom wall, said fourth side wall extending inwardly toward said opening and said fourth side wall having an outlet port defined therein;
        a first end wall connected to first ends of said first, second, third and fourth side walls; and
        a second end wall connected to second ends of said first, second, third and fourth side walls, said bottom wall, said first, second, third, and fourth side walls and said first and second end walls being connected so that said cavity is defined thereby;
    coagulant applying means for applying a coating of a coagulant to the material to be removed, said coagulant applying means including conduit means for providing a passageway by which said coagulant can be carried to said port defined in said fourth side wall for being discharged therefrom when said fourth side wall is moved adjacent the surface from which the material is to be removed; and
    withdrawing means, associated with said scraping means, for withdrawing the coagulant coated material which has been loosened from the surface which is scraped when said opening of said scraping means is moved adjacent the surface.

2. An apparatus for removing material from a surface, comprising:
    coagulant applying means for applying a coating of a coagulant to the material to be removed;
    scraping means, associated with said coagulant applying means, for scraping the surface to loosen the material therefrom, said scraping means having a cavity and an opening defined therein and including:
- a bottom wall;
- a first side wall extending from a first edge of said bottom wall;
- a second side wall extending from a second edge of said bottom wall disposed opposite said first edge of said bottom wall;
- an angular side wall extending from said second side wall so that said opening is defined between an unconnected edge of said angular side wall and an edge of said first side wall and in substantially the same plane as said angular side wall, said angular side wall having an outlet port defined therein through which said coagulant is dischargeable by said coagulant applying means;
- a first end wall connected to first ends of said first, second and angular side walls; and
- a second end wall connected to second ends of said first, second and angular side walls; and withdrawing means, associated with said scraping means, for withdrawing the loosened coagulant coated material from the scraped surface.

3. An apparatus for removing material from a surface, comprising:
- coagulant applying means for applying a coating of a coagulant to the material to be removed;
- scraping means, associated with said coagulant applying means, for scraping the surface to loosen the material therefrom, said scraping means having a cavity and an opening defined therein and including:
  - a neck member;
  - a first side wall connected to and extending away from said neck member at an obtuse included angle;
  - a second side wall connected to and extending away from said neck member at an obtuse included angle which is greater than the obtuse included angle between said first side wall and said neck member;
  - a first end wall connected to and extending from said neck member at an obtuse included angle and further connected between respective side edges of said first side wall and said second side wall so that an acute included angle is defined between said first side wall and said first end wall and so that an obtuse included angle is defined between said first end wall and said second side wall;
  - a second end wall connected to and extending from said neck member at an obtuse included angle and further connected between other respective side edges of said first and second side walls so that an acute included angle is defined between said second end wall and said first side wall and so that an obtuse included angle is defined between said second end wall and said second side wall; and
  - said first and second side walls and said first and second end walls terminating in a peripheral edge defining said opening so that said opening lies in a plane extending in angular relationship with respective surfaces of said first and second side walls; and withdrawing means, associated with said scraping means, for withdrawing the loosened coagulant coated material from the scraped surface.

* * * * *